(12) United States Patent
Lin

(10) Patent No.: US 6,488,875 B1
(45) Date of Patent: Dec. 3, 2002

(54) METHOD OF MANUFACTURING NO-STICK MULTI-COLOR INCENSE

(76) Inventor: Kun-Yu Lin, No. 36, Lane 60, Chai Cheng Rd., Hsintien City, Taiepi Hsien (TW)

( * ) Notice: Subject to any disclaimer, the term of this patent is extended or adjusted under 35 U.S.C. 154(b) by 260 days.

(21) Appl. No.: 09/611,966

(22) Filed: Jul. 6, 2000

(51) Int. Cl.$^7$ ............................................... B29C 47/04
(52) U.S. Cl. ................... 264/75; 264/211.11
(58) Field of Search ................ 264/75, 177.11, 264/211.11; 424/40

(56) References Cited

U.S. PATENT DOCUMENTS

| | | | |
|---|---|---|---|
| 2,532,349 A | * 12/1950 | Taylor et al. ................. 424/40 |
| 2,590,529 A | * 3/1952 | Gillies et al. ................. 422/29 |
| 2,606,858 A | * 8/1952 | Gillies et al. ................. 424/40 |
| 3,993,722 A | * 11/1976 | Borcher et al. ............. 264/102 |
| 4,092,388 A | * 5/1978 | Lewis ......................... 264/211 |
| 4,144,318 A | * 3/1979 | D'Orazio .................... 424/40 |
| 4,158,549 A | * 6/1979 | Martin .......................... 422/5 |
| 4,310,479 A | * 1/1982 | Ooms et al. ................ 264/101 |
| 4,515,768 A | * 5/1985 | Hennart et al. ............... 424/40 |
| 4,624,976 A | * 11/1986 | Amano et al. ............... 523/139 |
| 5,657,574 A | * 8/1997 | Kandathil et al. ............ 424/40 |
| 5,948,424 A | * 9/1999 | Kandathil et al. ............ 424/40 |

FOREIGN PATENT DOCUMENTS

| | | | |
|---|---|---|---|
| JP | 06-1714 | * 1/1984 |
| JP | 62-221618 | * 9/1987 |
| JP | 02-193912 | * 7/1990 |
| JP | 09-132518 | * 5/1997 |
| JP | 2000-1420 | * 1/2000 |

* cited by examiner

*Primary Examiner*—Mark Eashoo
(74) *Attorney, Agent, or Firm*—Jacobson Holman PLLC

(57) ABSTRACT

A method of manufacturing no-stick multi-color incense is to mix wood powder and an adhesive in powder form evenly and then the mixture is added into a liquid containing pigment and fragrance, stirred into a one-color glutinous paste and compressed into a single-color chunk by machines. The same procedures above-mentioned are repeated several times to obtain chunks with different colors. These mono-color chunks are cut into small cubes. The cubes are mixed together, piled on top of each other with different colors and then extruded by extruding machine to form incense with multiple colors. After drying, no-stick multi-color incense is obtained.

1 Claim, 1 Drawing Sheet

METHOD OF MANUFACTURING NO-STICK MULTI-COLOR INCENSE

BACKGROUND OF THE INVENTION

I. Field of the Invention

This invention relates generally to a method of manufacturing no-stick multi-color incense and, more specifically, to a method of manufacturing incense having two or more than two colors and a variety of shapes, which usually used in festivities, religious services or for other special purposes so that novelty and amusement are added to incense products and their market value can be enhanced.

II. Description of the Prior Art

Incense products are widely used in modern time. Especially for people from oriental culture, incense is adopted on various occasions, such as in memorial ceremonies, during meditation, or as insecticide. Incense products come with a stick or without a stick. No-stick incense has a variety of forms, such as incense coil, pastille, incense loop, and mini incense coil. Heretofore, almost all kind of incense has only one color. Incense with mono-color is lack of variety. It does not look appealing to consumers and thus restricts its value on the consumer market.

SUMMARY OF THE INVENTION

The present invention is directed to solving above-mentioned problems, and it is a primary object of the invention to provide an improved method of manufacturing no-stick multi-color incense which brings variety and novelty to incense products and is expected to boost the market value of incense.

In a method of manufacturing no-stick multi-color incense according to the present invention, no-stick incense with various colors is prepared. Wood powder and an adhesive in powder form are mixed evenly and then the mixture is added into a liquid containing pigment and fragrance. The solution is stirred into a one-color glutinous paste and is compressed into a chunk by machines. The same procedures above-mentioned are repeated several times to obtain chunks with different colors. These mono-color chunks are cut into small cubes. These cubes are mixed together, piled on top of each other with different colors and then extruded by extruding machine to form incense with multiple colors. After drying, no-stick multi-color incense is obtained.

With the method described above, each no-stick incense would be decorated with at least two colors. Whether the incense is in form of coil, pillar, or mini coil, the distinctive feature of colorfulness adds novelty and attractiveness that enhances product value and competitiveness on the consumer market.

DESCRIPTION OF THE PREFERRED EMBODIMENT

Figure 1:
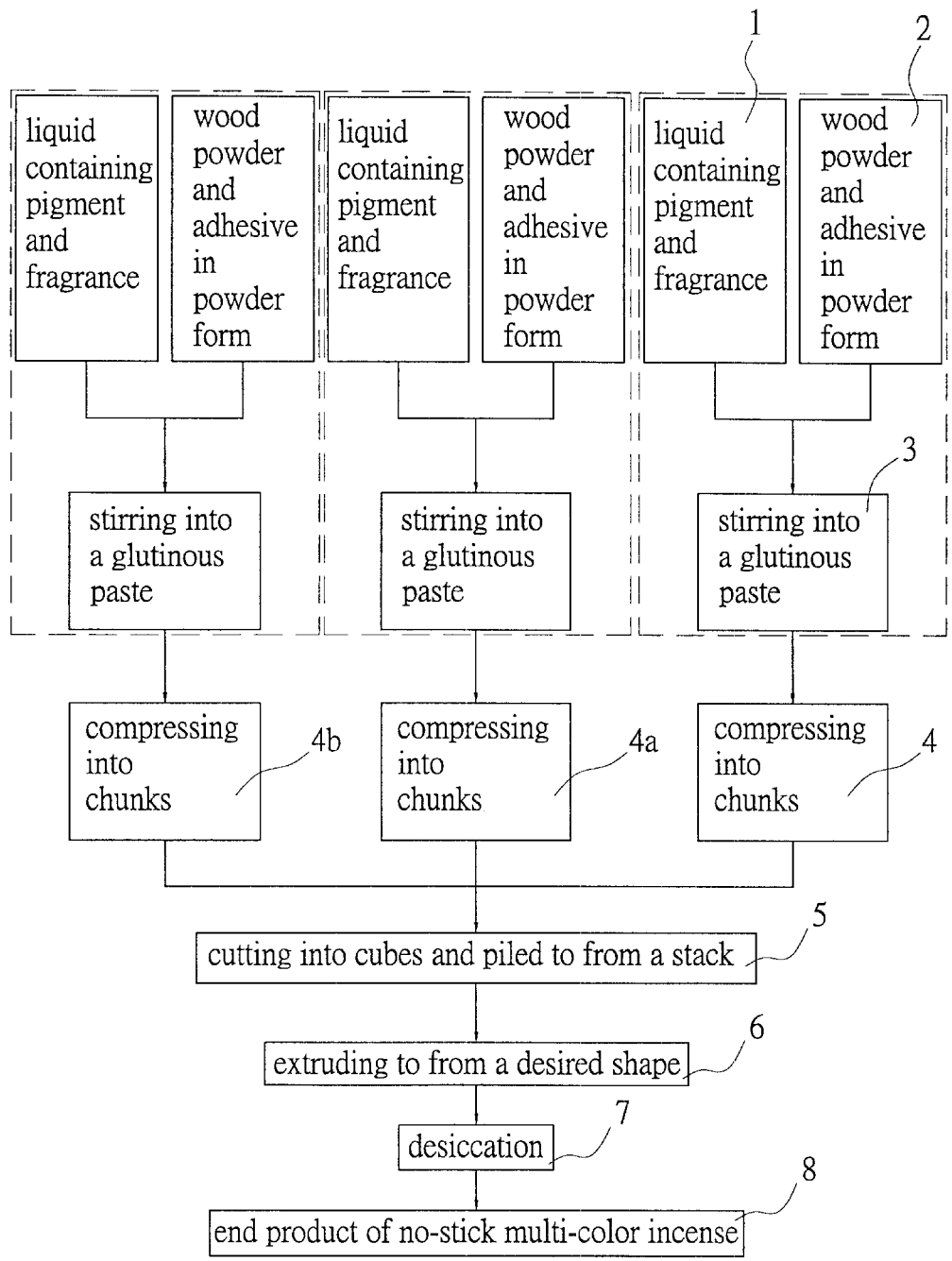
FIG. 1 presents the schematic diagram showing a process of manufacturing multi-color no-stick incense.

Refer to FIG. 1, the first step of the method of manufacturing no-stick multi-color incense is evenly mixing the wood powder and an adhesive in powder form 1. The mixture is added into a liquid 2 containing pigment and fragrance and stirred to obtain a single color glutinous paste 3. The glutinous paste 3 is compressed into a single chunk 4. Following the above-mentioned procedure repeatedly, another two mono-color chunks 4a, 4b are produced. All of these mono-color chunks 4, 4a, 4b are chopped into small cubes, and then are mixed up well. Then a certain number of cubes with different colors are piled to form a stack 5. The stack 5 is extruded 6 to obtain a desired shape of incense with multiple colors. After a period of desiccation 7, the end product of no-stick multi-color incense 8 is obtained.

The no-stick multi-color incense produced by this method would have a unique decorative function, competitiveness and novelty. This appealing feature is expected to enhance the product value and competitiveness on the consumer market.

Although the present invention has been described with respect to a preferred embodiment, it is contemplated that a variety of modifications, variations and substitutions may be done without departing from the scope of the present invention that is intended to be defined by the appended claims.

What is claimed is:

1. A method of manufacturing no-stick multi-color incense, comprising the steps of:

evenly mixing wood powder and an adhesive in powder form into a homogeneous mixture;

adding said mixture of said wood powder and said adhesive in powder form into a liquid containing a pigment of a single color and a fragrance;

stirring said mixture and said liquid into a single color glutinous paste;

compressing said single color glutinous paste into chunks;

repeating at least two additional times the steps of mixing, adding, stirring and compressing while changing a color of the pigment of said paste to obtain chunks of different single colors;

cutting said chunks of different single colors into small cubes;

irregularly mixing and piling up said small cubes of different single colors;

placing said irregularly mixed and piled small cubes of different single colors into an extruding machine;

extruding said small cubes of different single colors to form no-stick incense having a mixture of at least three different single colors; and drying said no-stick incense.

\* \* \* \* \*